United States Patent [19]

Owens et al.

[11] Patent Number: 5,302,093
[45] Date of Patent: Apr. 12, 1994

[54] DISPOSABLE CASSETTE WITH NEGATIVE HEAD HEIGHT FLUID SUPPLY AND METHOD

[75] Inventors: Dana J. Owens, Irving; Aaron Raines, Dallas; Ed G. Rasmussen; David J. Harrison, both of Carrollton; Carl R. Anderson, Dallas, all of Tex.

[73] Assignee: McGaw, Inc., Carrollton, Tex.

[21] Appl. No.: 877,618

[22] Filed: May 1, 1992

[51] Int. Cl.⁵ .................................. F04B 43/02
[52] U.S. Cl. .................... 417/474; 417/478; 417/479; 609/153
[58] Field of Search ........... 417/474, 478, 479; 604/153

[56] References Cited

U.S. PATENT DOCUMENTS

| 9,107 | 7/1852 | Ware | 92/101 |
|---|---|---|---|
| 4,142,524 | 3/1979 | Jassawalla et al. | 128/214 F |
| 4,155,362 | 5/1979 | Jess | 128/214 F |
| 4,199,307 | 4/1980 | Jasawalla | 417/474 |
| 4,236,880 | 12/1980 | Archibald | 417/478 |
| 4,276,004 | 6/1981 | Hahn | 604/153 |
| 4,322,201 | 3/1982 | Archibald | 417/279 |
| 4,382,753 | 5/1983 | Archibald | 417/479 |
| 4,391,600 | 7/1983 | Archibald | 417/478 |
| 4,410,322 | 10/1983 | Archibald | 417/478 |
| 4,548,607 | 10/1985 | Harris | 604/153 |
| 4,657,490 | 4/1987 | Abbott | 417/478 |
| 4,786,240 | 11/1988 | Koroly et al. | 417/413 R |
| 4,840,542 | 6/1989 | Abbott | 417/479 |
| 5,002,471 | 3/1991 | Perlov | 417/479 |
| 5,056,992 | 10/1991 | Simons et al. | 417/474 |

Primary Examiner—Richard A. Bertsch
Assistant Examiner—Peter Korytnyk
Attorney, Agent, or Firm—John W. Montgomery

[57] ABSTRACT

A fluid infusion pump includes a disposable cassette having an inlet, an outlet, and a fluid chamber between the inlet and the outlet. There is a fixed wall of the fluid chamber and a movable wall of the fluid chamber. A pump body receives the cassette in a fixed operating relationship such that an actuator in the pump body is activatable for reciprocal advancement and retraction with respect to the cassette and is adapted to confront the movable diaphragm when the cassette is received in the pump body. There is a detachable coupling between the actuator mounted in the pump body and the movable wall so that fluid is expelled from the fluid chamber on advancement of the actuator and positively drawn into the fluid chamber upon retraction of the actuator.

5 Claims, 6 Drawing Sheets

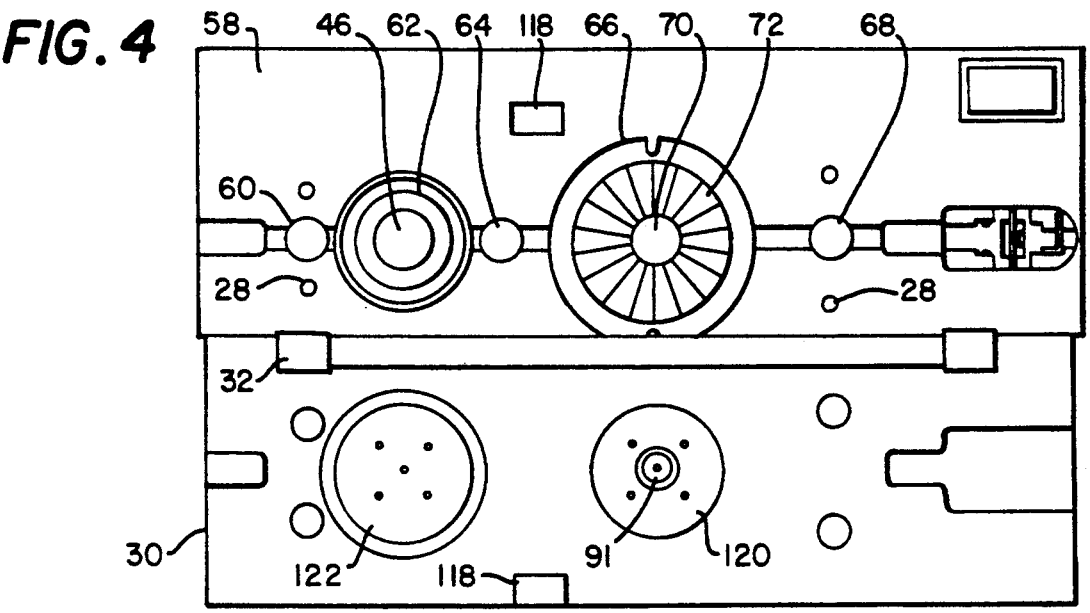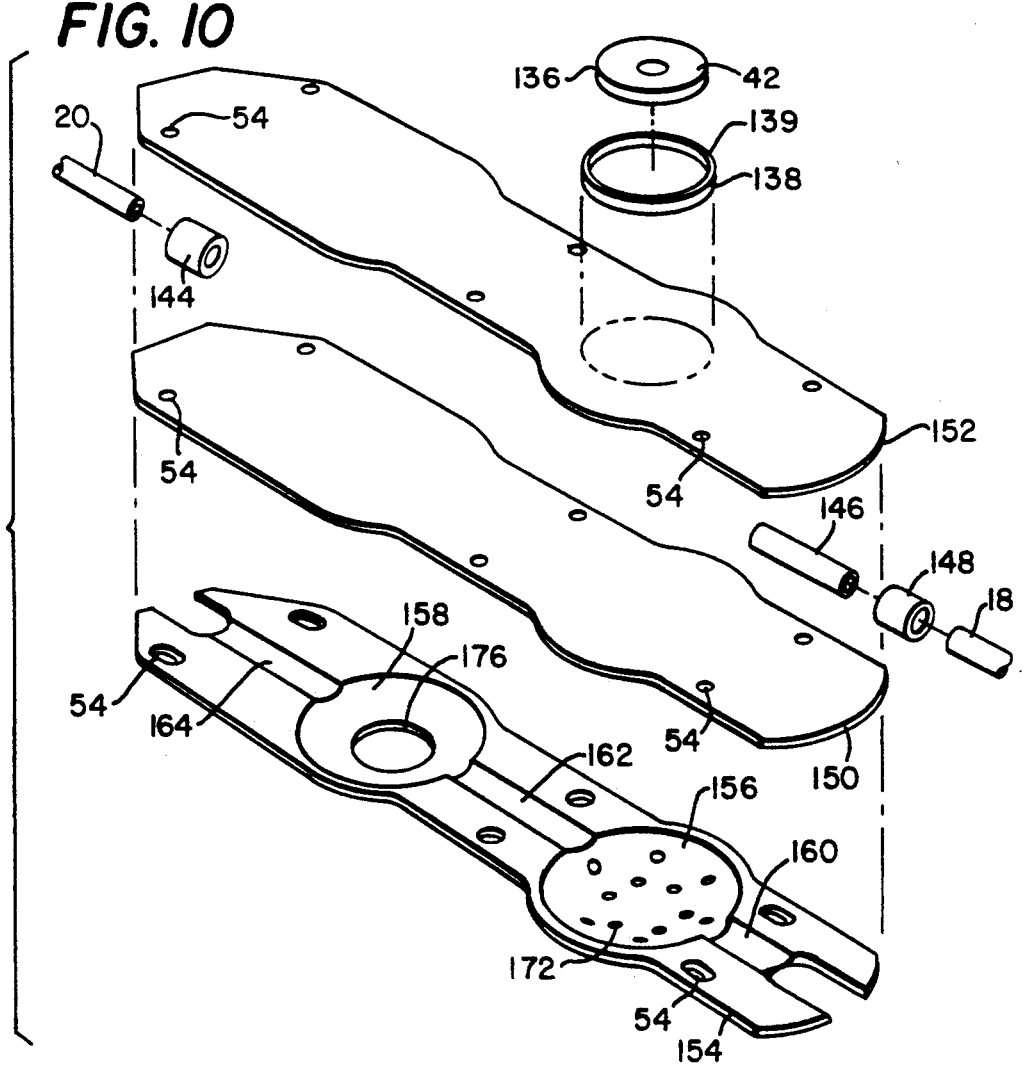

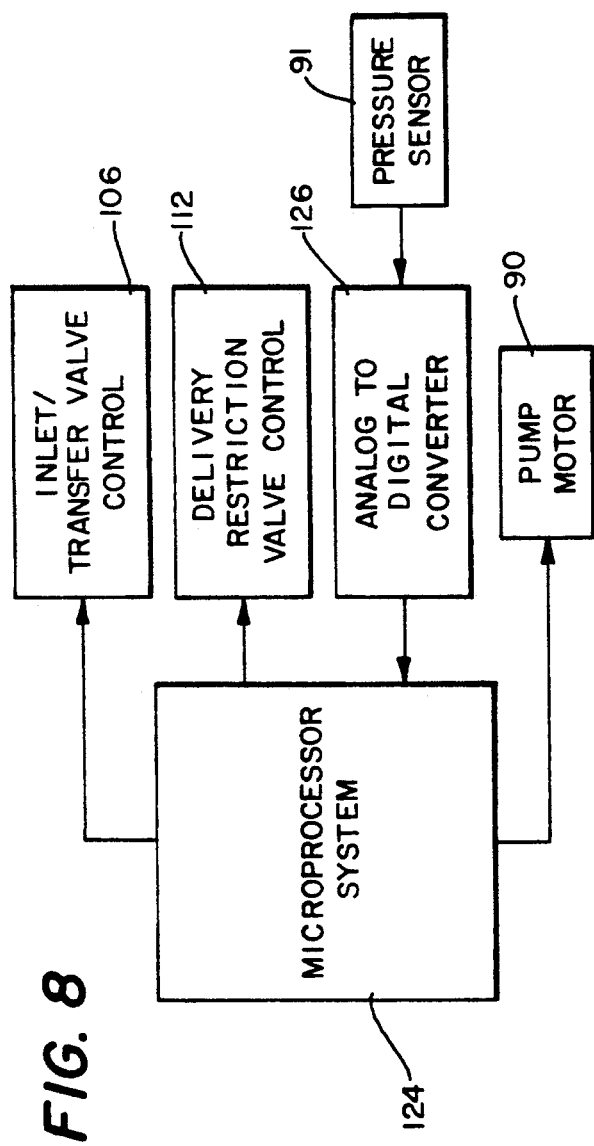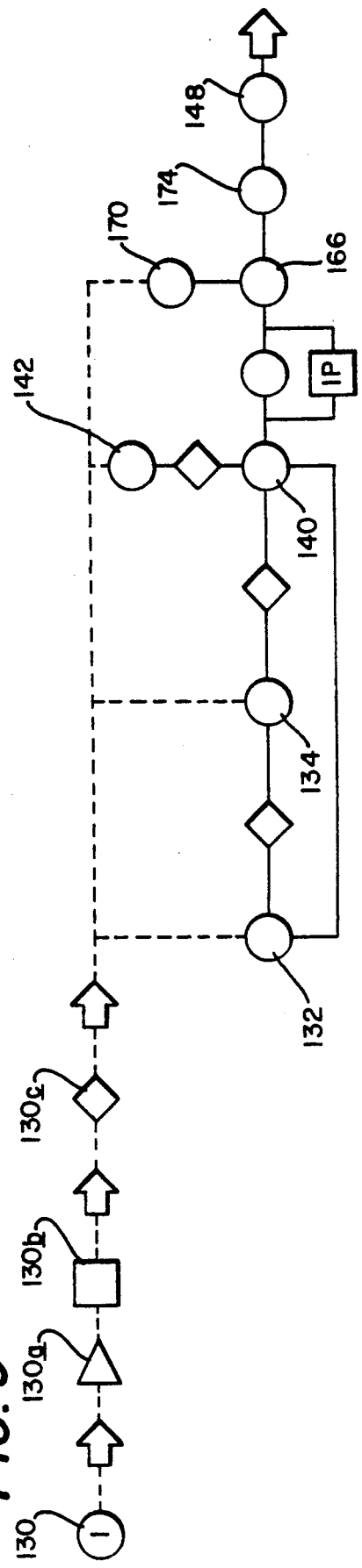
FIG. 8
FIG. 9

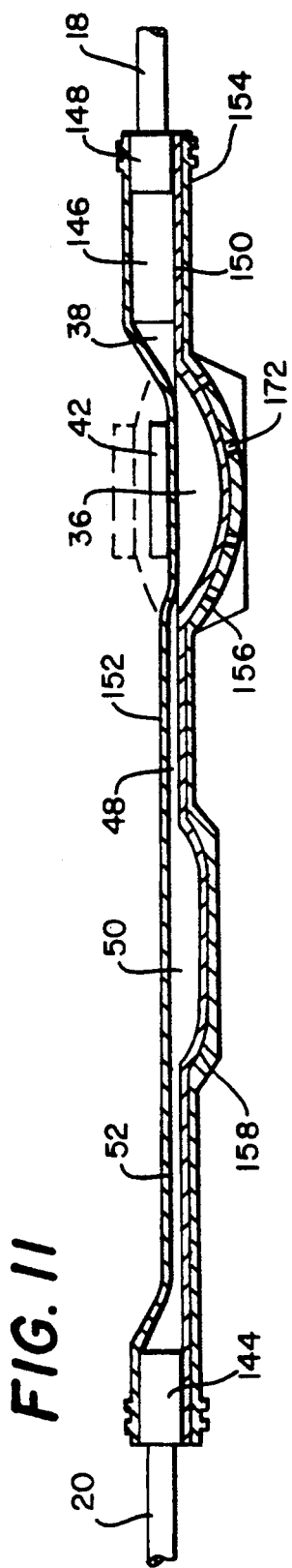
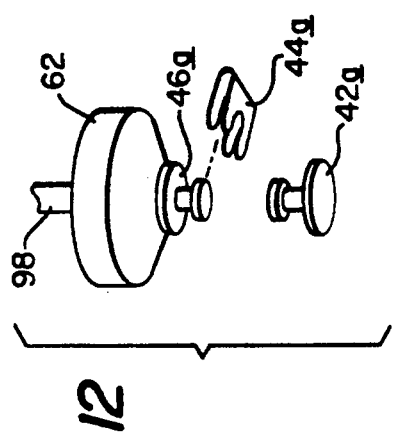
FIG. 11
FIG. 12

DISPOSABLE CASSETTE WITH NEGATIVE HEAD HEIGHT FLUID SUPPLY AND METHOD

TECHNICAL FIELD OF THE INVENTION

This invention relates to the delivery of a fluid to a patient by pressurizing the fluid, and in particular, to an infusion pump which provides fluid from a negative head pressure supply for delivery to a patient, which infusion pump incorporates an inexpensive disposable cassette.

BACKGROUND OF THE INVENTION

Infusion of fluids, such as drugs and plasma, into a patient is commonplace in the medical field. Two common infusion methods are intravenous delivery of fluids by gravity and either intravenous or intraarterial delivery by actually pumping the fluids for delivery to the patient.

In pump delivery, an infusion pump is used to pressurize the fluid. Past devices often require a complex cassette mechanism which comes into direct contact with the fluid to be delivered. Other devices require fluid to be fed by gravity to a pumping instrument having a cassette.

Peristaltic pumps acting upon in-line tubing segments have been used in this art. One example of a peristaltic pump, disclosed in U.S. Pat. No. 4,155,362, includes a back pressure valve to prevent gravity siphoning from the pumping chamber.

Another relatively simple pumping arrangement is disclosed in U.S. Pat. No. 4,142,524, in which a cassette is provided with inlet and outlet valves to and from a pumping chamber. The pump presses a rubber diaphragm on the cassette to diminish the volume of the cassette chamber by a known amount to deliver a predetermined quantity per pump stroke. An even simpler disposable element is disclosed in the pumping arrangement of U.S. Pat. No. 4,199,307, in which a pancake-shaped resilient pumping chamber is provided with upper and lower valves and an activating pumping piston which displaces a known volume on the pumping stroke. Yet another pump approach is disclosed in U.S. Pat. No. 4,322,201, which seeks to provide continuous, uninterrupted fluid flow by alternating between two pumping chambers, each of which employs the principle of the rolling diaphragm. A third rolling diaphragm chamber is employed for mechanically sensing pressure within the device for control purposes.

Another delivery pump system as disclosed in U.S. Pat. No. 4,657,490, employs a simple disposable element in combination with a relatively straightforward gravity supply and positive pumping action which is accurate and which provides pressure monitoring and self-checking diagnostics through measuring the pressure exerted on the pump actuator.

None of the foregoing art, however, provide a simple disposable element with a positive feed capable of drawing fluid from a negative head pressure supply in combination with simple straightforward delivery pumping action which is accurate and reliable and which provides improved reliability pressure monitoring through the cassette pumping membrane and self-check diagnostics.

SUMMARY OF THE INVENTION

One aspect of the present invention is a disposable cassette for use in medical infusion fluid pumping to positively draw fluid into the cassette for positive pumping to a patient. At least one pumping chamber in the cassette cooperates with a pumping instrument (in which it is operatively held) to draw fluid from a negative pressure fluid source or a negative head height without relying on positive head height gravity feed. The cassette is formed of two layers of flexible sheet material welded together and applied to a semi-rigid thin backing plate. Detachable connector means are provided in the area of the inlet chamber for drawing in fluid, which connector means are coupled to an actuator in the pumping instrument to which the cassette is inserted. The actuator is detachably coupled to the inlet chamber and upon retraction draws one wall of the chamber away from the other wall, thereby creating a negative pressure within the chamber to draw fluid through the inlet into the chamber. The inlet is closed with a first valve means pressing the inlet closed and the actuator advances against the chamber to decrease the volume of the chamber, forcing out fluid for eventual infusion to the patient. The positive supply of fluid allows a reliable amount of fluid to be available for infusion to the patient whether or not a supply source is above or below the infusion pump. The valve by which fluid is transferred out of the inlet chamber is closed, the inlet valve is opened, and the inlet actuator is withdrawn, so that the inlet chamber walls are moved back creating an increased volume and therefore, a negative pressure in the inlet chamber. The inlet chamber fills with fluid and the cycle can be repeated. When service to the patient is completed, or when the medicine is changed, the inlet actuator can be detached from the inlet chamber and the cassette can be removed and disposed while the relatively more complex pumping and mechanical valve system and instrument can be re-used without contamination. A new sterile cassette can be replaceably inserted and the inlet actuator can be coupled to the inlet chamber for use with a new patient or with a new infusion solution.

Another feature of the invention is the use of a magnetic coupling between the inlet chamber of the cassette and the inlet pumping actuator. A thin metal disk is attached to a flexible wall of the inlet pumping chamber which corresponds in location to a magnetic inlet actuator in the pumping instrument. The magnetic actuator secures itself to the flexible wall through magnetic coupling. The other wall of the inlet chamber of the disposable cassette is rigidified or otherwise restrained from moving toward the flexible wall. This allows the inlet pumping actuator to draw the flexible wall outward, thereby increasing the volume within the pumping chamber and drawing fluid into the cassette.

In accordance with another aspect of the present invention, a pumping chamber is provided in the disposable cassette which is distinct from the inlet chamber. Fluid is drawn into the inlet chamber which acts as a reservoir supply chamber or a refill chamber and is transferred from the inlet chamber into the outlet pumping chamber and is pumped to a patient for infusion. The disposable cassette has first and second flat flexible sheets defining the inlet and outlet chambers within the cassette, the inlet pumping chamber being variable in volume by the retraction or advancement of an inlet actuator, the outlet pump chamber being variable in volume as fluid fills the chamber or is pushed from it with an outlet actuator. The disposable cassette further has an inlet passage for movement of fluid into the inlet pump chamber, a transfer passage for moving fluid from the inlet pump chamber to the outlet pump chamber and an outlet passage for moving the fluid out of the outlet pump chamber. Also, inlet and outlet valves are provided for opening and closing the inlet and outlet, and a transfer valve is provided for opening and closing the transfer passage between the inlet pump chamber and the outlet pump chamber to control movement into the inlet pump chamber and from the inlet pump chamber into the outlet pump chamber. A carrier which is relatively rigid with respect to the first and second flat flexible sheets has an inlet concave depression which is attached to the outer surface of the first flexible sheet of the cassette. The first sheet layer is thereby securely affixed to the inlet concave depression, such that its movement is confined in both inward and outward directions. An outlet concave depression may also be defined in the relatively rigid carrier such that the outlet pumping chamber conforms to the outlet concave depression, and is confined in its movement at least in the outward direction. An inlet pumping actuator is provided for contacting and detachably coupling with the outer surface of the second sheet to deform the sheet by either compression or expansion between the second deformable sheet and the inlet concave depression and to thereby decrease or increase the volume of the inlet pumping chamber and to draw fluid into the inlet pumping chamber or to expel fluid into the outlet pumping chamber. An outlet pumping actuator is provided for contacting the outer surface of the second sheet at the outlet pumping chamber to deform the second sheet between the pumping member and the confining depression of the relatively rigid carrier to decrease the volume of the pump chamber and pump the fluid from the pumping chamber.

In accordance with another aspect of the present invention, a carrier having concave depressions for both the inlet and outlet pumping chambers further includes concave passage depressions which are substantially wider than the inlet passage, transfer passage, and outlet passage, as formed between two layers of flexible sheet. The concave passage depressions correspond in location to inlet, transfer and outlet valve mechanism in the pumping instrument, so that the criticality of the alignment of the passages with the closing valve mechanism is reduced and results in positive closure. An outlet or delivery valve may be provided for closing the outlet passage to a variable orifice size so that the valve mechanism gradually retracts to permit fluid flow from the pump chamber past the outlet valve when movement of the outlet pumping actuator pressurizes the fluid in the pumping chamber to a predetermined pressure. The outlet valve can be electronically controlled to allow the pressure in the pump chamber to be automatically controlled in a predetermined manner, as by controlling it to a constant pressure level selected by the user. The semi-rigid carrier may be provided with an orifice in the concave outlet depression, so that a sensor may be used to measure the fluid pressure in the pump chamber directly through the first flexible sheet, and can detect a lack of fluid, valve failure, and fluid obstructions.

BRIEF DESCRIPTION OF THE DRAWINGS

A more complete understanding of the invention may be had by reference to the following detailed description and claims when taken in conjunction with the accompanying drawings, wherein like elements are represented by like numerals and wherein:

FIG. 4 is a schematic front view of the pump prior to insertion of the disposable cassette according to the present invention;

FIG. 8 is a schematic diagram of a microprocessor control circuit;

FIG. 9 is a schematic process flow diagram of the method of construction according to the present invention;

FIG. 10 is a perspective view schematically depicting the assembly construction of the cassette according to the present invention;

FIG. 11 is a side cross-sectional view taken along line 11—11 of the cassette assembly of FIG. 2; and FIG. 12 is a schematic assembly view of an alternative embodiment of a coupling mechanism according to the present invention.

DETAILED DESCRIPTION OF THE PREFERRED EMBODIMENTS

Figure 1:
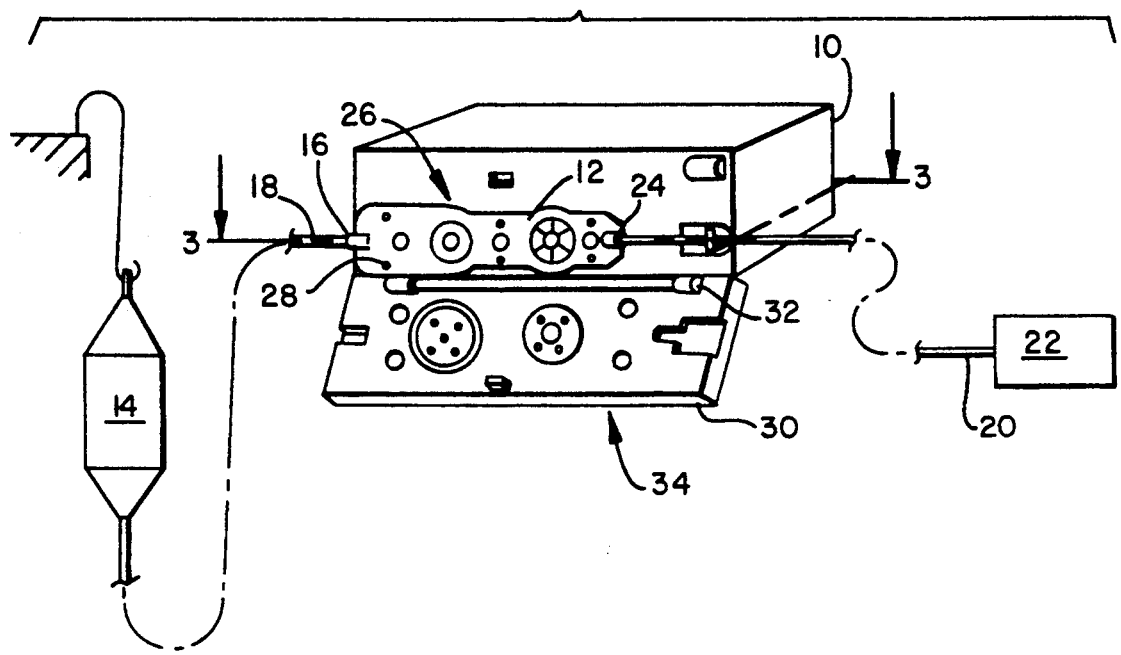
FIG. 1 is a schematic representation of an infusion pump forming one embodiment of the present invention.

As illustrated in FIG. 1, the pumping system is composed of a pumping instrument 10 in which a disposable cassette 12 is mounted for operation. The supply container 14 containing the fluid to be infused may be positioned above or below the cassette 12 and is connected to inlet 16 of cassette 12 by means of tubing 18. Outlet tubing 20 extends to the patient 22 from the outlet 24 of cassette 12.

At the front of the instrument body 10 is a cassette receiving and actuating section 26, including cassette positioning pins 28. A closable door 30 is pivotable about hinges 32 for replaceably holding the cassette 12 within the cassette receiving section 26 properly aligned as with alignment pins 28 for operational confrontation between the cassette and the pumping instrument. A data display/operator input panel 34 may be formed on the front of instrument body 10 and preferably is formed on the front of closable door 30 for display of operational data and for operator input while the cassette is held in place by closure of door 30. The details of the actuator receiver section will be more fully explained below with reference to FIGS. 3 and 4.

Figure 2:
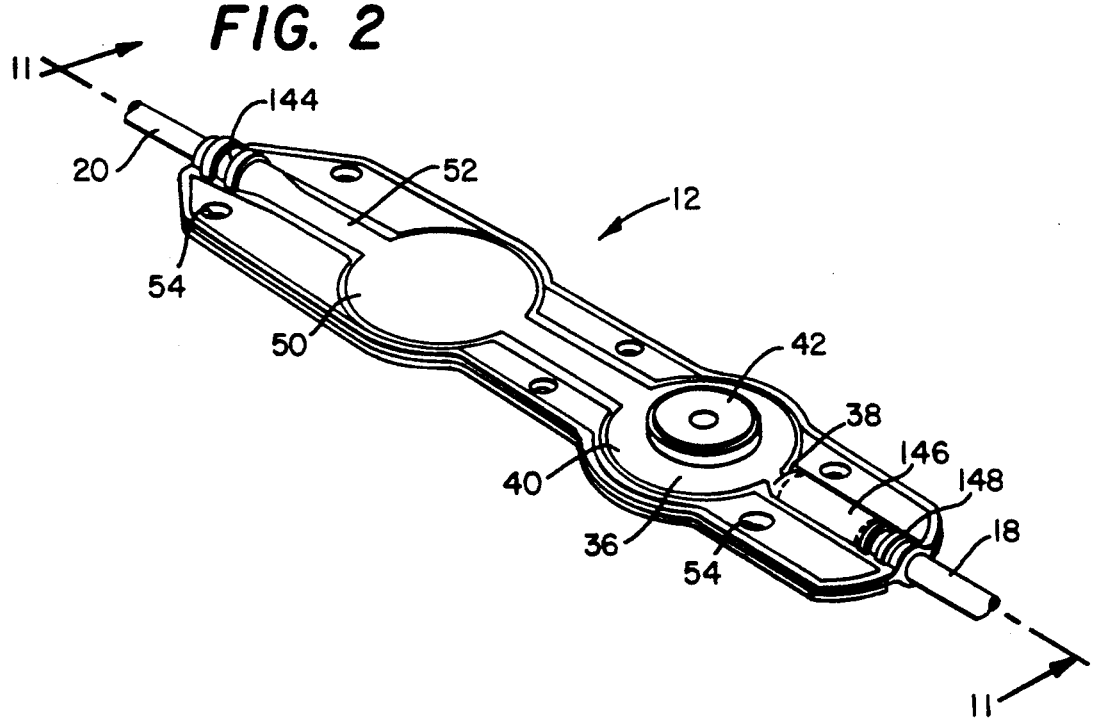
FIG. 2 is a perspective view of a disposable cassette according to one embodiment of the present invention.

A preferred embodiment of the disposable cassette assembly 12 is shown in a top plan view in FIG. 2. The cassette has an inlet chamber 36 which is in fluid communication with inlet 16 through inlet passage 38. One wall 40 of inlet chamber 36 is flexible, and forms a flexible wall 40 having affixed thereto a portion 42 of a detachable coupling mechanism 44.

In the embodiment of the disposable cassette 12, shown in a perspective view in FIG. 2, the portion 42 of the coupling mechanism 44 is a magnetically attractable disk, such as a metal disk which is affixed to flexible wall 40. As will be more fully understood with reference to FIG. 3, disk 42 couples with magnet 46 which is attached to inlet pumping actuator 62 and forms the second portion of detachable coupling mechanism 44. Fluid is received into inlet chamber 36 through inlet passage 38 and is transferred out of inlet chamber 36 through transfer passage 48 and outward from the cassette through outlet 22.

Preferably, the cassette 12 also defines an outlet pumping chamber 50 which receives fluid through transfer passage 48 and from which fluid is pumped through outlet passage 52 to outlet 22 and is delivered by tube 20 to the patient. As will be more fully explained below in connection with the construction of the cassette assembly 12 as set forth in FIGS. 9 through 11, alignment holes 54 are formed for alignment during the construction of the cassette assembly and also for alignment during installation of the cassette assembly within the cassette receiving and actuation section 26 of the pumping instrument 10.

Figure 3:
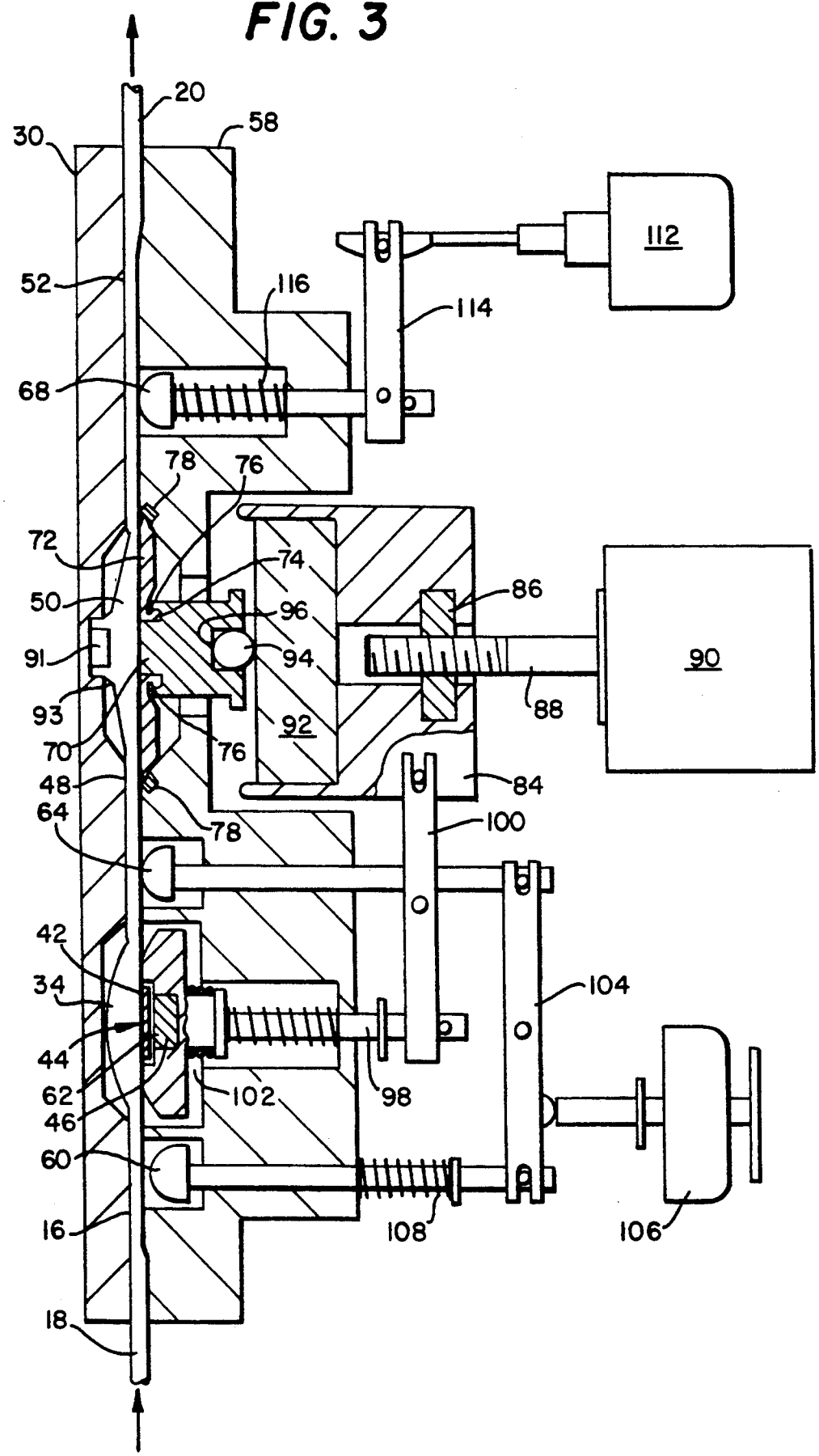
FIG. 3 is a cross-sectional view of the infusion pump of FIG. 1 taken along a horizontal plane through a center line of an installed disposable cassette.

The details of construction of the cassette receiver actuator section 26 are best illustrated in FIGS. 3 and 4. FIG. 3 is a cross-sectional view of pumping body 10 taken along a horizontal plane through the pumping instrument and disposable cassette. FIG. 4 is a front view of the cassette receiving section 26 of the pump 10 prior to mounting the disposable cassette 12. The moving members which confront and act upon cassette 12 when it is in an operating position are arrayed on panel 58 secured to the instrument body 10. Proceeding from upstream, the major elements are inlet valve 60, inlet actuator 62, transfer valve 64, outlet pumping member 66, and outlet valve 68.

Figure 5:
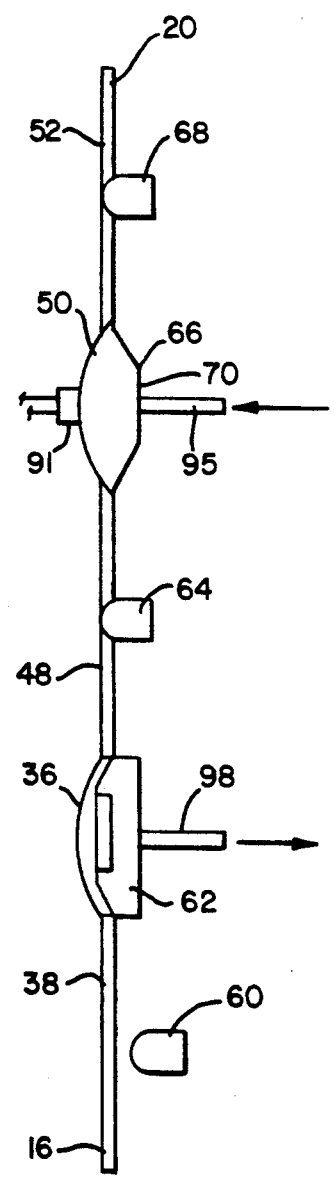
FIGS. 5, 6, and 7 illustrate schematically the operational sequence of an infusion pump according to one embodiment of the present invention.
Figure 6:
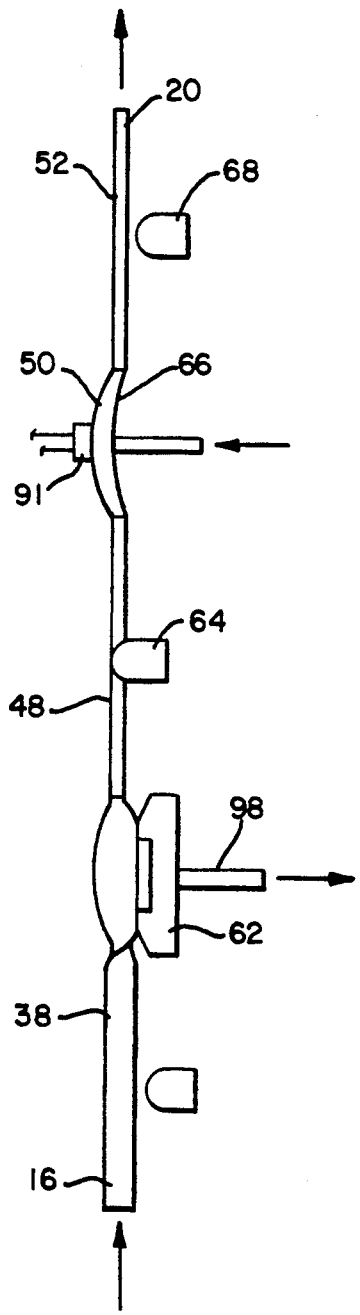
Figure 7:
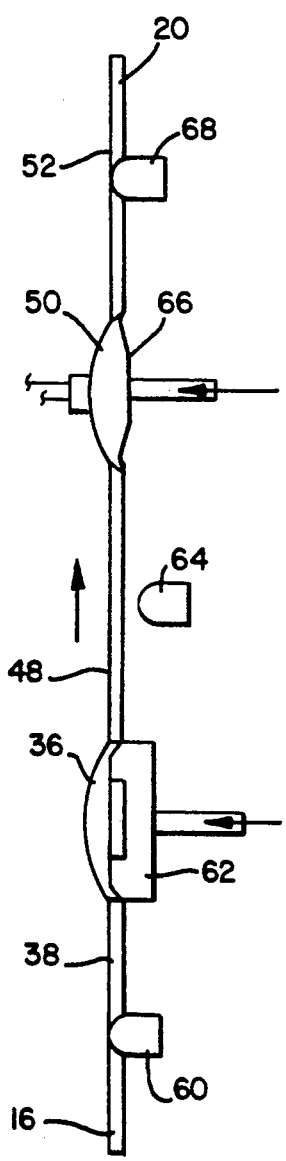

The outlet pumping assembly 66 preferably includes a central hub 70 surrounded by a plurality of petal-shaped sections 72 to form the movable pressing surface which produces pumping pressure in the outlet pumping chamber of the disposable cassette 12. The hub 70 may be formed by press fit of a male hub member and a female hub member. A circular recess 74 near the outer edge of hub 70 is formed between the male and female hub members. Each petal section 72 is provided on the rear face of its inner end with a smooth hook-shaped curve portion 76 which corresponds to a smooth curve provided on the hub recess 74. The inner edge of each petal section 72 is pivotally retained in the hub recess 74, with the complementary smooth curves of each member permitting relative pivotal movement of each petal-shaped section with respect to the hub about an axis perpendicular to recess 74. The instrument body panel 58 is provided with an annular recess that circumferentially surrounds petal nest 78, which retains the outer end of each petal-shaped section 72. The confronting surfaces of petal nest 78 and the outer end of each petal-shaped section 72 are also shaped for smooth pivoting of the petal-shaped sections with respect to the instrument body. A movable carriage 84 is mounted behind hub 70 and carries a drive nut 86 which is engaged with the threads of a threaded motor shaft 88 rotated by stepper motor 90. The forward end of carriage 84 may be recessed to receive a load cell 82 which has its central force measuring diaphragm confronting a metal ball 94 retained in a rear central recess 96 formed on hub 70. Preferably, however, a pressure sensor 91 is positioned and carried in door 30 for direct contact against the second wall 93 of the outlet pumping chamber 50 of cassette 12. The pressure sensor 91 will have improved pressure reading accuracy over a load cell 82 because of its substantially direct access to pressure chamber 50 without sensing frictional variations due to variable sliding conditions of pumping actuator 70 and associated movement of petals 72. Also, a more direct pump actuation may be accomplished with the door-mounted pressure sensor 91, as the load cell 82 and associated metal ball 94 may be replaced with a continuous connector shaft 95 as schematically depicted in FIGS. 5 through 7, from stepper motor 90.

Rotation of stepper motor 90 acts through the cooperation of threaded motor shaft 88 and the carriage nut 86 to drive carriage 84 forward. This action transmits force to hub 70 moving the hub forward. The translational motion of hub 70 also causes each petal-shaped section 72 to pivot near each of its ends. The petal assembly thus forms a truncated cone of varying height as the hub moves between the extreme retracted position and advanced position, as depicted in FIGS. 5 and 6.

Inlet actuator 62 is carried forward by refill shaft 98 which is either advanced forwardly or retracted rearwardly through lever 100 acted upon by carriage 84. Thus, as viewed in FIG. 3, when carriage 84 is moving forwardly to push the outlet pump assembly 66 forward, the action of refill lever 100 causes shaft 98 and inlet pump member 62 to be withdrawn, withdrawing metal disk 42 and inlet pump chamber diaphragm 40 with it. As motor 90 is driven in the opposite direction to withdraw carriage 84, lever 100 allows the inlet pumping member 62 to move forward. Spring 102 biases member 62 to its forward position and thus carriage 84 to the rearward direction.

Inlet valve 60 and transfer valve 64 have rounded surfaces for engaging the flow path of the cassette 12 and are operated in tandem fashion through inlet valve lever 104 driven by solenoid 106. When one of the two valves is in the open or rearward position, the other is necessarily in the closed or forward position. Preferably, the parts are assembled so that in the middle of the path of travel of valve lever 104, both valves 60 and 64 are closed to insure no bypassing of fluid. Bias to inlet valve lever 104 is provided by spring 108 surrounding the inlet valve shaft, which biases the arrangement to the condition of inlet valve 60 open, transfer valve 64 closed.

Outlet valve 68 is operated by a stepper motor 112 acting upon delivery lever 114 and is biased to the closed position by spring 116. The linear stepper motor 112 is capable of positioning the delivery restriction valve 68 in any selected position from fully retracted or open position as shown, to a fully extended or closed position. This permits the output from outlet pumping chamber to be metered according to the selected opening position of the delivery restriction valve 68.

As indicated previously, actuator panel 58 is provided with mounting pins 28 corresponding to the alignment in mounting holes 54 in cassette 12. The actuator door 30 is mounted to panel 58 by hinges 32 and is closed by latch 118. As a double check for patient safety, opening of door 30 will stop pumping and sound an alarm. In the inner face 110 of door 30, concave depression 120 is arranged to confront petal assembly 66 when the door is closed, and similar concave depression 122 confronts the refill actuator 62. Depressions 120 and 122 may be provided with air vent holes through the front door to facilitate closing the door with cassette 12 in position. With the cassette mounted on pins 28, the inlet fluid chamber 36 and the outlet pump chamber 50 are captured between the inlet actuator 62 and outlet member 66 and the depressions 122 and 120, respectively. In the operating position, valve 60 is adjacent inlet passage 38 to close off the inlet when the valve member 60 is extended. Likewise, valve 64 may be activated to close off transfer passage 48.

The delivery valve 68 may be activated to selectively close outlet passage 52 to an orifice of any desired size. The pumping compartment defined between the rigid wall of depression 120 and the outlet pump petal assembly 66 is filled by the fluid from an inlet chamber 36 when the petal assembly 66 is in its retracted position, and the outlet pump chamber 50 is bulged with fluid at a low fluid pressure of approximately ten (10) inches of water. The volumetricity of pumping is then provided by the accuracy of volume displaced between the extreme positions of outlet pump assembly 66 and the compliance of the exterior wall of outlet pump chamber 50 to the moving truncated cone surface presented by petal pump assembly 66.

As will be discussed more fully below, the material used to construct the cassette is flexible, and therefore conforms to the surface of the petal elements so that the position of the petal assembly defines the volume of fluid enclosed between it and the rigid surface on the other side very precisely. The volumetric performance of this arrangement is defined almost completely by the movement of the hub 70 and thus, the petal-shaped sections 72 and not by the mechanical properties of the disposable cassette element which is confined from movement. The volume displaced by the petal assembly varies in a linear fashion with translational movement of hub 70.

As illustrated in FIG. 8, the system is operated under the control of a microprocessor system 124. The microprocessor controls the movement of solenoid 106 between two positions: (1) inlet valve open, transfer valve closed, and (2) inlet valve closed, transfer valve open. Likewise, microprocessor 124 controls delivery valve stepper motor 112 to select the total or partial restriction imposed by delivery valve 68 on the cassette outlet passage 52. Microprocessor 124 also selects, in accordance with the rate selected by the operator on input panel 34, the rate of movement of the pumping stepper motor 90. Continuous control over operation, diagnostics and aberrant conditions are principally provided by either a load cell 82, which measures the force being exerted on pumping assembly 66, or by pressure sensor 91 which directly measures the pressure in the outlet pump chamber 50, as exerted by petal assembly 66. As indicated previously, a door-mounted load cell 91 is preferred for accurate pressure measurement. This data is continuously provided to microprocessor 124 or through analog to digital converter 126.

A typical cycle of operation is illustrated in FIGS. 5 through 7. FIG. 5 illustrates the condition of the actuator and disposable cassette as the delivery portion of the cycle has begun. At this stage, the outlet pump chamber 50 has been completely filled with fluid to occupy the compartment formed between the cassette outlet chamber depression and the fully retracted petal assembly 66. Delivery valve 68 and transfer valve 64 are closed, completely capturing the fluid in outlet pump chamber 50. Inlet valve 60 is opened while the transfer valve 64 is closed, so that fluid may be drawn into the inlet fluid chamber 36 as inlet actuator 62 is retracted. The microprocessor begins the initial stage of the delivery cycle by directing the outlet pump stepper motor 90 to advance to begin pressurization of fluid in outlet pump chamber 50. During the first few steps of stepper motor operation, valves 68 and 64 remain closed to permit this initial pressurization. Elevation of the pressure caused by the advancement of petal assembly 66 is sensed by pressure sensor 91 which data is fed to microprocessor 124. This serves as a diagnostic to verify the capturing of a full load of fluid in the outlet pump chamber 50. A failure to pressurize in the first several steps of motor 90 indicates a system problem. It could be that the fluid supply is depleted, so that the outlet pump chamber 50 has not been filled, or that the inlet actuator mechanism has not appropriately filled inlet supply chamber 36. Another possibility is that a defect in valve 64 or 68 is permitting fluid to leak from chamber 50. In any of these events, operation of the instrument will be stopped by the microprocessor 124 and an alarm sounded.

If, however, normal pressurization occurs, microprocessor 124 instructs delivery valve 68 to open as motor 90 advances, to deliver fluid to the patient through outlet 24, as illustrated in FIG. 6. Continuous monitoring of the pressure sensor 91 permits the microprocessor to exercise continuous control over delivery valve 68 to selectively restrict the outlet passage 52. This permits the device to insure that the delivery rate is not higher than the requested rate, as for example, where gravity siphoning occurs. The microprocessor is also programmed with a selected maximum pressure limit, set by the user through display/input panel 34, which is used in continuous pressure monitoring. Escalation of pressure above the selected maximum pressure even with the delivery valve 68 wide open, will result in alarm and shut-down of the instrument, indicating that there is some condition which requires nursing attention, and that fluid is not reaching the patient. The ability to select a maximum pressure limit by the user permits relatively rapid alarms, even at relatively low selected infusion rates.

Preferably, the microprocessor is programmed to maintain a relatively constant pressure in outlet pump chamber 50 by selected restriction of delivery valve 68, such constant pressure being just below the maximum pumping pressure selected by the operator. This is helpful in insuring that there are no variations in volumetric delivery which might result from operation at varying pumping pressures.

While fluid is being delivered by advancement of petal assembly 66, the inlet actuator 62 is automatically being withdrawn, transfer valve 64 is already closed, pulling with it flexible wall 40 through coupling 44, and fluid is drawn by negative pressure into the inlet chamber 36 through open inlet passage 38. When the outlet pumping assembly 66 has reached its full extended position, inlet and outlet valves 60 and 68 close and transfer valve 64 opens. Microprocessor 124 then reverses stepper motor 80 for rapid retraction of petal assembly 66 and a rapid extension of inlet actuator 62 as illustrated in FIG. 7. This permits a very quick transfer of fluid into outlet pump chamber 50 which will arm the device for the next delivery cycle. During the outlet pumping portion of the delivery cycle, energy was stored in spring 102 immediately behind the inlet pumping member 62. This energy is used to effect the transfer of fluid so as to drastically reduce the mechanical loading on the main pump motor. The purpose of this is to allow an increased motor speed during the fluid transfer step which in turn reduces the time taken to effect the transfer as it is principally limited only by the maximum operating speed of the main outlet pump motor 90. Once the transfer of fluid is complete, valve 60 opens and valve 64 closes, and the system is in a condition once more indicated in FIG. 5. A mechanical stop on shaft 98 limits the amount of movement of the inlet refill actuator 62 so as to avoid pumping any fluid back towards the fluid container 14 as valve 60 opens.

With reference to FIG. 9, in conjunction with FIGS. 10 through 11, the construction and construction process of a preferred embodiment of a disposable cassette assembly according to the present invention will be more fully understood.

The construction materials, which generally include thin sheet place film, molded plastic carrier plates or moldable plastic for forming plastic carriers, magnetically attractable disks or sheet metal for forming disks, tubing, and an adhesive, are received, as schematically represented by numeral 130. The receiving step may include staging for inspection and quality control 130a, inspecting 130b, and moving the received material to a storage area 130c. The flexible portion of the cassette comprises two sheets 150 and 152 of flexible film such as PVC sheets, which are cut or blanked at step 132 to an appropriate length and shape corresponding to the pump receiving and holding section. Typically, the flexible PVC film is received in rolls which are de-reeled, placed under pressure, punched or cut to an appropriate shape, and placed in a container for use in the next step. A portion 42 of the coupling mechanism 44 is then welded to a second sheet 152 of the film at step 134. In the preferred embodiment, a flat metallic disk 42 is formed in a flat circular shape having a perimeter ledge 136 therearound. Disk 42 is welded to a shallow plastic tray 138, as shown in FIG. 10. Preferably, plastic tray 138 has a rim 139 which surrounds and overlaps ledge 136 as it is welded to the disk 42 as by ultrasonic welding. Disk 42 with the plastic tray affixed thereto is positioned on the second film strip and welded to the film strip in step 140.

Other detachable coupling mechanisms could be similarly welded in step 140. For example, a mechanical clip 44a is depicted in FIG. 12 which connects to a pair of clip receptors 42a and 46b which are attached to the cassette and the inlet actuator, respectively. Such an alternative clip could be advantageous for purposes of specialized Nuclear Magnetic Resonance (NMR) or Magnetic Resonance Imaging (MRI) fluid infusion. However, the simplicity of the magnetic coupling is normally preferred.

At step 142, tubing is cut. An appropriate length of outlet tubing 20 is cut. An outlet connector plug 144, which is a larger diameter tube and which receives outlet tube 20 is cut. A short section of flexible support tubing 146 is cut for insertion into inlet passage 38. An inlet plug connector tubing 148 is cut and an appropriate length of supply tube 18 is cut. The outlet tubing 20 is inserted into the outlet connector plug 144; the flexible support tube 146 is inserted partially into the inlet connector plug; and, the supply tube 18 is partially inserted into the opposite end of the inlet connector plug.

As shown in FIG. 10, the inlet and outlet tubing assemblies are placed in alignment between the first sheet 150 and the second flexible sheet 152 to which the metal disk has been welded. The sheets 150 and 152 are sandwiched about the aligned tubing and welded together to thereby sealingly connect each of the flexible sheets to the outlet connector plug and the inlet connector plug and to define a sealed fluid path through the cassette, including an inlet passage 38, an inlet pumping chamber 36, a transfer passage, an outlet pumping chamber, and an outlet passage. The inlet passage has a portion thereof immediately adjacent the inlet chamber which is narrower than the remainder of the inlet passage to thereby hold the inserted flexible support tube 146 within the inlet passage without permitting it to slide into the inlet chamber. The flexible support tube 146 has sufficient resiliency to advantageously prevent collapse of the inlet passage 38 due to the negative pressure caused during the drawing back of the flexible wall 40 of the inlet chamber 36. Fluid from supply tube 18 freely flows into the inlet chamber 36 without being restricted by a collapsed inlet passage 38. The support tube 146 is sufficiently flexible to permit complete closure by inlet valve 60, although it has been found that small amounts of leakage at the inlet valve are not critical because of the rapid rate of the transfer from the inlet chamber 36 to the outlet pumping chamber 50.

With reference to both FIGS. 10 and 11, a preferred carrier plate 154 is formed having concave indentations 156 and 158 for receiving the inlet chamber and outlet pumping chamber. The carrier plate is rigid, relative to the flexible sheets 150 and 152, and may be composed of a plastic, such as PVC, which has a thickness several times greater than that of the flexible sheets. Also formed in the carrier plate 154 are indented troughs or channels 160, 162, and 164 corresponding in location to the inlet, transfer and outlet passages. The troughs or channels are shallow, having a radius of curvature 165 corresponding to that of the valves 60, 62, and 64 and are substantially wider than the width of the passages 38, 48 and 52. The welded flexible sheet portion is aligned through locating holes 54 and corresponding locating holes 54a on the carrier plate 154. The width of the channels allow tolerance in the alignment with the passages which facilitates manufacture without adversely affecting the functionality of the cassette.

The construction method as in FIG. 9 of the disposable cassette assembly as shown in FIG. 10 includes the step 166 of welding the flexible portion of the cassette to the rigid carrier. Prior to welding, an adhesive material 168, such as one which can be cured by ultraviolet (UV) radiation, is applied at step 170 to the inlet chamber concave depression 156. The layered flexible assembly is located and welded in place at step 166. Subsequently, a negative pressure is applied through vent holes 172 to the depression 156 to draw the second flexible layer 152 against the concave depression 156. Ultraviolet radiation is applied at step 174 to cure the adhesive while it is drawn firmly against the depression wall. Alternatively, a positive pressure could be applied to the opposite side of the flexible sheets adjacent the depression, either internal to the two flexible sheets or externally to the first flexible sheet to which the metallic disk is welded. The negative pressure is preferred as it avoids potential contamination by pressurization inside the cassette and also avoids potential uneven pressure due to pressing through the magnetic disk.

The outlet pumping chamber cavity has an orifice 176 formed therein through which the door mounted pressure load cell 91 may sense the pumping pressure directly through the second thin flexible sheet 152 of cassette 12.

It will be appreciated that the cassette and instrument could be designed without separate input and output pumping chambers, and that a single pumping chamber activatable both for drawing supply fluid in from a negative head pressure, and pumping the fluid positively to the patient through a metered control valve could be constructed, without departing from certain aspects of the present invention. However, it is believed that improved reliability, improved diagnostic monitoring, and improved control are advantageously achieved using an input pumping chamber to draw fluid from a supply without regard to positive or negative head height of the supply, in combination with a separate outlet pumping chamber which can be carefully monitored directly through the exterior flexible wall thereof to accurately monitor and apply pressure to the patient.

Although specific embodiments of the invention have been illustrated in the accompanying drawings and described in the foregoing detailed description, it will be understood that the invention is not limited to the embodiments disclosed, but is capable of numerous rearrangements, modifications, and substitutions of parts and elements without departing from the spirit of the invention. It is intended that the scope of the invention disclosed herein be limited only by the broadest interpretation of the appended claims to which the inventors are legally entitled.

What is claimed is:

1. A disposable cassette for use in an infusion pumping instrument of the type having an inlet valve, an inlet fluid actuator, a transfer valve, an outlet fluid actuator, an outlet valve and means for replaceably holding a disposable cassette, said disposable cassette comprising:
   (a) first and second flexible sheets sealed along interior surfaces defining an inlet passage, an inlet fluid chamber, a transfer passage, an outlet fluid chamber, an outlet passage and means for locating said defined passages and fluid chambers adjacent corresponding valves and fluid actuators in said pumping instrument;
   (b) a relatively rigid carrier to which an exterior surface of said first flexible sheet is attached and having concave indentations correspondingly sized and located for receiving said inlet fluid chamber and said outlet fluid chamber and for constraining movement of said first flexible sheet thereinto; and
   (c) means operatively associated with said inlet fluid chamber for expanding the volume of the inlet fluid chamber corresponding to retraction of the inlet fluid actuator away from the cassette and for decreasing the volume of the inlet fluid chamber corresponding to advancement of said inlet fluid actuator against said cassette, wherein said means for expanding the volume of said inlet fluid chamber comprises a magnet rigidly affixed to said inlet actuator and a magnetically attractable disk rigidly affixed to said second sheet at the inlet fluid chamber so that the magnet on the actuator and the disk on the cassette are magnetically coupled for moving said second sheet apart from said first sheet in the inlet fluid chamber upon retraction of said inlet actuator.

2. A disposable cassette for use in an infusion pumping instrument of the type having an inlet valve, an inlet fluid actuator, a transfer valve, an outlet fluid actuator, an outlet valve and means for replaceably holding a disposable cassette, said disposable cassette comprising:
   (a) first and second flexible sheets sealed along interior surfaces defining an inlet passage, an inlet fluid chamber, a transfer passage, an outlet fluid chamber, an outlet passage and means for locating said defined passages and fluid chambers adjacent corresponding valves and fluid actuators in said pumping instrument;
   (b) a relatively rigid carrier to which an exterior surface of said first flexible sheet is attached and having concave indentations correspondingly sized and located for receiving said inlet fluid chamber and said outlet fluid chamber and for constraining movement of said first flexible sheet thereinto; and
   (c) means operatively associated with said inlet fluid chamber for expanding the volume of the inlet fluid chamber corresponding to retraction of the inlet fluid actuator away from the cassette and for decreasing the volume of the inlet fluid chamber corresponding to advancement of said inlet fluid actuator against said cassette wherein said means for expanding the volume of said inlet fluid chamber includes:
     (i) detachable coupling means having a first portion thereof rigidly affixed to said inlet actuator, having a second portion thereof rigidly affixed to the second sheet at the inlet chamber, and having a magnetic coupling between the inlet actuator and the second sheet interactive between the first and second portion with coupling force, so that the second sheet is pulled away from the first sheet upon retraction of the inlet actuator and so that the interactive mechanism can be manually separated for replacement of the disposable cassette; and
     (ii) means for affixing an exterior surface of said first sheet to the concave depression in said relatively rigid carrier so that it is not drawn with the retraction of the second sheet at the inlet fluid chamber.

3. A disposable cassette for use in an infusion pumping instrument of the type having an inlet valve, an inlet fluid actuator, a transfer valve, an outlet fluid actuator, an outlet valve and means for replaceably holding a disposable cassette, said disposable cassette comprising:
   (a) first and second flexible sheets sealed along interior surfaces defining an inlet passage, an inlet fluid chamber, a transfer passage, an outlet fluid chamber, an outlet passage and means for locating said defined passages and fluid chambers adjacent corresponding valves and fluid actuators in said pumping instrument;
   (b) a relatively rigid carrier to which an exterior surface of said first flexible sheet is attached and having concave indentations correspondingly sized and located for receiving said inlet fluid chamber and said outlet fluid chamber and for constraining movement of said first flexible sheet thereinto; and
   (c) means operatively associated with said inlet fluid chamber for expanding the volume of the inlet fluid chamber corresponding to retraction of the inlet fluid actuator away from the cassette and for decreasing the volume of the inlet fluid chamber corresponding to advancement of said inlet fluid actuator against said cassette wherein said means for expanding the volume of said inlet fluid chamber includes:
     (i) detachable coupling means having a first portion thereof rigidly affixed to said inlet actuator, having a second portion thereof rigidly affixed to the second sheet at the inlet chamber, and having a removably attachable mechanical clip and corresponding clip receptors on the second sheet and the inlet actuator interactive between the first and second portion with coupling force, so that the second sheet is pulled away from the first sheet upon retraction of the inlet actuator and so that the interactive mechanism can be manually separated for replacement of the disposable cassette; and (ii) means for affixing an exterior surface of said first sheet to the concave depression in said relatively rigid carrier so that it is not drawn with the retraction of the second sheet at the inlet fluid chamber.

4. A disposable cassette for use in an infusion pumping instrument of the type having an inlet valve, an inlet fluid actuator, a transfer valve, an outlet fluid actuator, an outlet valve and means for replaceably holding a disposable cassette, said disposable cassette comprising:

(a) first and second flexible sheets sealed along interior surfaces defining an inlet passage, an inlet fluid chamber, a transfer passage, an outlet fluid chamber, an outlet passage and means for locating said defined passages and fluid chambers adjacent corresponding valves and fluid actuators in said pumping instrument;

(b) a relatively rigid carrier to which an exterior surface of said first flexible sheet is attached and having concave indentations correspondingly sized and located for receiving said inlet fluid chamber and said outlet fluid chamber and for constraining movement of said first flexible sheet thereinto, wherein said relatively rigid carrier further comprises:

(i) a shallow inlet trough having a concave cross-sectional shape and sized wider than said inlet passage as defined by said first and second flexible sheets so that alignment of said passages in said troughs is simplified;

(ii) a shallow transfer trough having a concave cross-sectional shape and sized wider than said transfer passage as defined by said first and second flexible sheets so that alignment of said passages in said troughs is simplified;

(iii) a shallow outlet trough having a concave cross-sectional shape and sized wider than said outlet passage as defined by said first and second flexible sheets so that alignment of said passages in said troughs is simplified; and (iv) said inlet, transfer and outlet valves sized and shaped corresponding to the width and shape of the troughs so that complete closure by the corresponding valves is facilitated; and (c) means operatively associated with said inlet fluid chamber for expanding the volume of the inlet fluid chamber corresponding to retraction of the inlet fluid actuator away from the cassette and for decreasing the volume of the inlet fluid chamber corresponding to advancement of said inlet fluid actuator against said cassette.

5. A method of constructing a disposable cassette for use in an infusion pumping instrument of the type having an inlet valve, a pumping element, an outlet valve, and a disposable cassette receiving and holding section, said method comprising the steps of:

(a) cutting first and second thin flexible sheets of plastic material in a shape for operative association in the receiving and holding section of the infusion pumping instrument;

(b) welding a magnetically retractable disk to the exterior surface of the second thin flexible sheet of plastic material;

(c) welding the first and second thin flexible sheets together to define therebetween a fluid path comprising an inlet passage, a fluid chamber corresponding to the location of the disk, and an output passage, which inlet and outlet passages are in fluid communication with the fluid chamber and are welded to the inlet and outlet cut tubing;

(d) forming alignment holes exterior to the fluid path in the welded plastic film sheets (e) forming a carrier plate sized corresponding to the size of the cut film sheets and defining a concave fluid chamber depression; and (f) bonding the welded film sheets to the carrier plate, including bonding the first sheet to the concave fluid chamber depression to rigidly hold the first sheet opposite the welded disk at the fluid chamber so that the second sheet can be independently drawn away from the first sheet to increase the volume in the fluid chamber.

* * * * *